United States Patent
Sakai et al.

(10) Patent No.: US 7,501,257 B2
(45) Date of Patent: Mar. 10, 2009

(54) MOLECULAR DIAGNOSTIC METHOD OF A CANCER TISSUE OR A CANCER CELL

(75) Inventors: Toshiyuki Sakai, Kyoto (JP); Hideki Ishihara, Mino-gun (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 382 days.

(21) Appl. No.: 10/547,072

(22) PCT Filed: Feb. 25, 2004

(86) PCT No.: PCT/JP2004/002164

§ 371 (c)(1),
(2), (4) Date: Oct. 27, 2005

(87) PCT Pub. No.: WO2004/076686

PCT Pub. Date: Sep. 10, 2004

(65) Prior Publication Data

US 2007/0031813 A1      Feb. 8, 2007

(30) Foreign Application Priority Data

Feb. 26, 2003     (JP) ............................. 2003-048653

(51) Int. Cl.
*C12Q 1/48* (2006.01)
(52) U.S. Cl. ...................................................... 435/15
(58) Field of Classification Search .................... 435/15
See application file for complete search history.

(56) References Cited

U.S. PATENT DOCUMENTS

| | | | | |
|---|---|---|---|---|
| 5,672,508 A * | 9/1997 | Gyuris et al. | ............ | 435/320.1 |
| 5,914,249 A * | 6/1999 | Lal et al. | .................... | 435/69.1 |
| 6,048,693 A * | 4/2000 | Bitter | ........................... | 506/10 |
| 2003/0064426 A1* | 4/2003 | Poole et al. | ..................... | 435/8 |
| 2003/0134315 A1* | 7/2003 | Warenius et al. | ............... | 435/6 |
| 2004/0126784 A1* | 7/2004 | Hitoshi et al. | .................. | 435/6 |

FOREIGN PATENT DOCUMENTS

| | | |
|---|---|---|
| EP | 1233060 A2 | 8/2002 |
| JP | 1233 060 A2 * | 8/2002 |
| JP | 2002-335997 A | 11/2002 |
| WO | WO 97/04316 A1 | 2/1997 |
| WO | WO 99/42090 A2 | 8/1999 |
| WO | WO 99/42821 A2 * | 8/1999 |
| WO | WO 99/42828 A2 | 8/1999 |
| WO | WO 99/42834 A2 | 8/1999 |
| WO | WO 99/42835 A1 | 8/1999 |
| WO | WO 99/42837 A1 | 8/1999 |
| WO | WO 00/01845 A3 * | 1/2000 |

OTHER PUBLICATIONS

Salh B. et al. Differential Cyclin Dependent Kinase Expression and Activation in Human Colon Cancer. Anticancer Research 19(1B)741-748, Jan./Feb. 1999.*
Kim J. et al. Amplified CDK2 and cdc2 Activities in Primary Colorectal Carcinoma. Cancer 85(3)546-553, 1999.*
Yamamoto H. et al. Coexpression of cdk2/cdc2 and Retinoblastoma Gene Products in Colorectal Cancer. British J of Cancer 73, 1231-6, 1995.*
Li K. et al. Activation of Cyclin Dependent Kinases CDC2 and CDK2 in Hepatocellular Carcinoma. Liver 22(3)259-268, 2002.*
Baljinder Salh, et al, "Differential Cyclin-Dependent Kinase Expression and Activation in Human Colon Cancer", Anticancer Research, vol. 19, 1999, pp. 741-748.
H. Yamamoto, et al, "Coexpression of cdk2/cdc2 and Retinoblastoma Gene Products in Colorectal Cancer", British Journal of Cancer, vol. 71, 1995, pp. 1231-1236.
Jong Hun Kim, et al Amplified CDK2 and cdc2 Activities in Primary Colorectal Carcinoma, Cancer, vol. 85, No. 3, 1999 pp. 546-553.
K. Li, et al, Activation of Cyclin-Dependent Kinases CDC2 and CDK2 in Hepatcellular Carcinoma, Liver, vol. 22 2002, pp. 259-268.
L.A. Seabra, et al, "Wild Type CDK1 and CDK4 Proteins Are Co-Elevated in Human Cancer", Proceedig of the America Association for Cancer Research, vol. 39, 1998, p. 442.
J.S. Breslin, et al, "Expression of the Cyclin-Dependent Kinase cdk4 in Perinatal and Adult Rat Lung", American Journal of Respiratory Cell and Molecular Biology, vol. 9, 1993, pp. 533-540.
Ishihara H., et al. *A New Cancer Diagnostic System Based on a CDK Profiling Technology.* Biochim Biophys Acta. Sep. 25, 2005;1741(3):226-33.

* cited by examiner

*Primary Examiner*—Ralph Gitomer
(74) *Attorney, Agent, or Firm*—Sughrue Mion, PLLC (57) ABSTRACT

The present invention relates to a more accurate method of diagnosing cancer in a tissue or a cell by measuring the expression and activity of cell cycle related proteins and analyzing a cell cycle profile. In a cell cycle profile, at least two values of expression or activity of cell cycle related proteins are concurrently measured. The measurement of the cell cycle related protein is not limited as to the measurement method.

14 Claims, 4 Drawing Sheets

MOLECULAR DIAGNOSTIC METHOD OF A CANCER TISSUE OR A CANCER CELL

TECHNICAL FIELD

The present invention relates to a profiling method of a tissue and a cell by simultaneously measuring cell cycle related proteins on multi parameters, and specifically, relates to a molecular diagnostic method of a cancer tissue or a cancer cell.

BACKGROUND ART

Cancer cells are characterized by unlimited proliferation. If means for selectively inhibiting proliferation of cancer cells without impairing the proliferation ability of normal cells can be found, termination of tumor growth is enabled irrespective of extent of differentiation or penetration of the tumor, or degree of metastasis. Development of anticancer agents targeting for proliferating cells has been extensively carried out to provide a therapeutic drug of cancer. However, such anticancer agents have involved significant problems of accompanying cell toxicity because they also inhibit the proliferation of normal cells.

In an attempt to solve such problems, it is interesting to comprehend as to how division of cancer cells differs from that of normal cells.

Cell proliferation according to a cell cycle is determined by a holoenzyme formed by a combination of a protein called cyclin, the concentration of which varies through the cell cycle, and cyclin dependent kinase (hereinafter, referred to as "CDK") which is converted into its active form upon binding. Further, the holoenzyme which is a cyclin/CDK complex is inhibited by a protein called cyclin dependent kinase inhibitor (hereinafter, referred to as "CDKI") including a protein p21 WAF1/CIP1 (p21).

Various studies have been conventionally made on proteins of cyclin E gene, D gene and B1 gene, and CDK that corresponds to each cyclin dependent kinase. Cyclin/CDK2 complex and cyclin D/CDK4 or cyclin D/CDK6 complex control cell cycle progress through cell cycle checkpoint during the G1 phase and the S phase that is a DNA synthesis phase. Also, cyclin B1/CDK1 complex controls cell cycle checkpoint immediately before mitosis.

An invention relating to a diagnostic method and therapeutic method of cancer focusing attention to the aforementioned cyclin/CDK complex has been already disclosed in Japanese Translation Provisional Publication Nos. 2002-504683 and 2002-519681, and a method of measuring a cell cycle regulation factor without using a radioactive isotope (hereinafter, referred to as "RI") has been also disclosed (Japanese Patent Provisional Publication No. 2002-335997).

When the state of G1 phase in a cell cycle is disrupted, abnormal cell proliferation is induced. A p53 molecule (tumor suppressing molecule) has been known as a protein playing a central role in mainly controlling the G1 phase of a cell cycle. It has been already reported that mutation in the p53 gene is caused at a high incidence rate in a variety of cancer tissues. A normal p53 molecule functions as a transcription factor, and controls cell proliferation, DNA repair, differentiation, and apoptosis. Moreover, in noncancerous cells having a damaged DNA, the p53 molecule promotes expression of p21 cip1/kip1 that is a CDKI molecule, suppresses endogenously existing CDK2 kinase activity, and arrests the cell cycle at the restriction (R) point on the boundary of G1/S phase. On the other hand, mutated p53 molecules can not regulate the cell cycle, but lead to proliferation of uncontrollable cells and instability of a genome, resulting in the cell turned into a malignant tumor.

A series of molecular pathological investigations have elucidated clinical significance of a CDK controlling molecule in the G1 phase. Over expression of cyclin E corresponding to CDK2 that is a cell cycle regulatory protein and cyclin D1 corresponding to CDK4 and CDK6, and inactivation of CDKI molecules, e.g., p21 corresponding to CDK2, p27 corresponding to CDK2, 4 and 6 and p16 corresponding to CDK2 are playing important roles in tumor formation in various tissues.

However, on the grounds of unestablished immunohistological techniques depending on specificity for each antibody and the like, ratios of expression of these cyclin E, cyclin D1 and the like in cancer tissues greatly vary with respect to each report.

DISCLOSURE OF THE INVENTION

An object of the present invention is to provide a more accurate diagnostic method of a tissue and cell for carrying out definite diagnosis of cancer, drug resistance test and prognosis.

The present inventors focused attention on the presence of a relationship between existence of various types of cell cycle regulation factors and the state of a cancer cell. As a result of elaborate investigations, it was found that more accurate diagnosis of cancer is enabled by measuring the expression and activity of cell cycle related proteins, and analyzing a cell cycle profile. Thus, the present invention was accomplished.

Accordingly, the present invention is directed to:

1. A method of the examination of a tissue and/or a cell which comprises measuring at least two or more kinds of cell cycle related proteins, and carrying out cell cycle profiling;

2. The method of the examination according to the above item 1 wherein the cell cycle profiling is to obtain the information of the tissue and/or the cell by analyzing, on the basis of a measurement value of one cell cycle related protein, another relative measurement value;

3. The method of the examination according to the above item 1 wherein the cell cycle related protein is cyclin dependent kinase;

4. The method of the examination according to the above item 2 wherein the cell cycle related protein is at least two or more selected from any one of CDK1, CDK2, CDK4 and CDK6;

5. The method of the examination according to the above item 2 wherein one measurement parameter of the cell cycle related protein which makes the basis is a CDK1 activity value;

6. The method of the examination according to the above item 1 wherein the measurement of the cell cycle related protein comprises the measurement of expression of cyclin;

7. The method of the examination according to the above item 1 wherein the cell cycle related protein is a cyclin dependent kinase inhibitor;

8. A method of the examination of cancer which comprises carrying out the method of the examination of a tissue and/or a cell according to the above item 1; and 9. A system of the examination for the method of the examination according to the above item 1.

BEST MODE FOR CARRYING OUT THE INVENTION

In the present invention, the term "cell cycle related protein" means a factor which can regulate a cell cycle, and specifically, a factor which can accelerate or arrest the cell cycle in a cycle starting from division of a cell until the next division once again. Examples of such a factor include e.g., cyclin, cyclin dependent kinase (CDK), as well as cyclin dependent kinase inhibitor (CDKI) and the like.

Moreover, in the present invention, the term "cell cycle profiling" means concurrent measurement of a minimum of 2 or more, preferably 3 or more values of expression or activity of cell cycle related proteins. Preferably, the term means to obtain the information (profile) on states or properties of a tissue and cell to be a target of the measurement by analyzing, on the basis of a measurement value of one cell cycle related protein, another relative measurement value. Examples of the measurement parameter include e.g., CDK activities such as CDK1 activity, CDK2 activity, CDK4 activity and CDK6 activity; CDK expression such as CDK1 protein expression, CDK2 protein expression, CDK4 protein expression and CDK6 protein expression; cyclin expression such as cyclin B protein expression, cyclin D protein expression and cyclin E protein expression; CDKI expression such as p16 protein expression, p21 protein expression and p27 protein expression; p53 protein expression; Rb protein expression and the like.

Furthermore, the reference value for obtaining the relative value may be, for example, a CDK1 activity value or a CDK1 protein expression value, however, a measurement value other than the above parameters may be also used.

(Measurement of Cell Cycle Related Protein)

For the measurement of the cell cycle related protein conducted in the method of the examination of the preset invention, any measurement method which has been known or is going to be developed in future can be employed. For example, the CDK enzyme activity can be measured using conventional radioactive isotope (RI), or can be also used without using RI (Japanese Patent Provisional Publication No. 2002-335997). In the site of clinical examination, it is preferred that the measurement is conducted with a method in which RI is not used for readily and quickly measuring on a tissue collected from multiple patients or the like by biopsy, surgical resection or the like.

Furthermore, for the measurement of the amount of protein expression, any measurement method which has been known or is going to be developed in future can be employed. For example, the measurement can be conducted with a simple quantitative analysis system based on a dot blot technique by way of a protein expression analysis.

(Preparation of Sample for Cell Cycle Profiling)

For carrying out the method of the examination according to the present invention, preparation of a sample for the measurement is required. As a specific method of solubilization of a cell and a method of isolation of a sample containing CDK, those described in Japanese Patent Provisional Publication No. 2002-335997 may be employed.

(Analysis of Cell Cycle Profiling)

In normal cells, cell proliferation is strictly controlled by a regulation factor in the G1 phase. On the other hand, progress of the cell cycle after passing through the restriction point (R) is mildly controlled in comparison with the G1 phase. Therefore, it is reasonable to carry out profiling of the G1 phase CDK (CDK2, 4, 6) activity on the basis of the G2/M kinase or CDK1 activity value.

Grounds for abnormal proliferation of cancer cells can not be simply analyzed with expression of a cell cycle related protein. Accordingly, in addition to alteration of the amount of expression of the protein, mutation or the like of the molecule has been reported as a cause of inactivation or activation of these molecules. It is difficult to determine various causes as described above with a primary assay system. Thus, it was believed that measuring the CDK activity, the regulation of which involves many of cell cycle related proteins, is useful in diagnosis of cancer.

In Table 1, clinicopathological features of patients suffering from gastrointestinal cancer determined in the Examples described below are shown. Median age of the studied group was 65 years old (in the range of from 23 years to 86 years old). One among 22 cases of large intestine cancer, five among 8 cases of stomach cancer, and three among 7 cases of esophagus cancer were in the clinical stage of IV phase.

Kinase activities of four kinds of CDK and expression results of nine kinds of cell cycle related proteins in normal mucosal tissues and cancer tissues derived from colon cancer patients in Table 2 and Table 3, from stomach cancer patients in Table 4 and Table 5, and from esophagus cancer patients in Table 6 and Table 7 are shown. Furthermore, results of analysis of each CDK in cancer tissues and normal mucosal tissues are shown in Table 8.

In Table 2 to Table 7, to the measurement value beyond [mean value+2SD (standard deviation)] is appended the sign of (+), while to the measurement value less than [mean value−2SD] is appended the sign of (−). The measurement was conducted according to the process in Examples described below.

The expression of CDK was for CDK1, which exhibited a higher value in three kinds of the cancer tissues of: large intestine, stomach and esophagus, in comparison with normal mucosa. When cut off value of the amount of CDK1 expression per total protein was determined as [mean value in corresponding normal tissue+2SD], the value was 1.99 ng/μg in colon, 1.60 ng/μg in stomach, and 0.91 ng/μg in esophagus.

When analysis was carried out using this cut off value, it was decided that the expression of CDK1 is positive in 27% of tissues of colon cancer (6/22), 75% of tissues of stomach cancer (6/8), and 57% of tissues of esophagus cancer tissue (4/7). These differences were all statistically significant (large intestine; $P<0.05$, stomach; $P<0.05$, esophagus; $P<0.05$, with a Wilcoxon signed-rank test).

To the contrary, statistically significant difference was not found between cancer tissues and normal tissues for the expression of CDK2, 4 and 6.

Among CDK activities, marked difference was found for CDK2 between cancer tissues and normal tissues (colon; $P<0.01$, stomach; $P<0.01$, esophagus; $P<0.01$, with a Wilcoxon signed-ranks test).

When cut off value of the CDK2 activity per weight of protein was determined for each tissue as [mean value of the CDK2 activity exhibited in the normal tissue+2SD], the value was 0.054 U/μg in large intestine, 0.102 U/μg in stomach, and 0.033 U/μg in esophagus. Accordingly, 72% of tissues of large intestine cancer (16/22), 75% of tissues of stomach cancer (6/8), and 100% of tissues of esophagus cancer tissue (7/7) were decided to be positive. For example, in connection with breast cancer, it was reported that expression of an isoform of cyclin E having an excessive activity strongly correlates to survival rate of patients. This correlation suggests that high CDK2 activity is a major cause of instability of the genome and malignant alteration of cancer.

With respect to CDK4 activity and CDK6 activity, lower value was observed in cancer tissues compared to those in normal mucosa (large intestine; CDK4 $P<0.05$, large intestine; CDK6 $P<0.05$, with a Wilcoxon signed-ranks test).

In the stomach tissue, higher expression and activity was found for both CDK1 and CDK2 compared to other organs. These results suggest that the mucosal tissue in stomach regenerate more actively than other organs, or thickening and proliferation owing to infection with Helicobacter Pyroli often found in Japanese may be suggested.

Technical scope of the present invention encompasses reagents and examination systems used in methods of tissue examination and methods of cell examination; methods of cancer examination by way of the present method of the examination; and therapeutic drugs and therapeutic methods of cancer which were selected by analyzing the profile.

Hereinafter, the present invention is explained in detail with reference to Examples, however, the present invention is not limited thereto.

EXAMPLE 1

Method of Cell Examination

1) Preparation of Tissue Sample for Measurement

Each surgically collected tissue (2 mm$^3$) was ground with a lysis buffer containing Nonidet P-40 (NP-40) (manufactured by Calbiochem), and solubilized with a homogenizer. Insoluble substances were removed by a filter. Thus resulting cell lysate was employed as a tissue sample for the measurement.

2) Measurement of CDK Activity

A sample containing 100 μg of the total protein was added to 2 μg of an antibody (anti-CDK1, 2, 4 and 6 antibodies, manufactured by Santa Cruz) and 20 μl of protein A beads (manufactured by BioRad) to allow them to react at 4° C. for 1 hour and to precipitate CDK molecules.

After washing with a buffer (0.1% NP-40, 50 mM Tris-HCl, pH 7.0) three times, 50 μl of a substrate mixture containing proteins was added thereto followed by incubation at 37° C. for 10 minutes while shaking.

The substrate mixture contains 10 μg of histone H1 corresponding to CDK1 and CDK2 (manufactured by Upstate Biotechnology, Inc.), 10 μg of C-terminal domain of recombinant Rb protein corresponding to CDK4 and 5 (a.a. 769-921), 5 mM adenosine-5'-O-(3-thiotriphosphate) (ATP-γS, manufactured by Sigma Corporation, USA), and buffer (20 mM Tris-HCl, pH 7.4, 0.1% Triton X-100).

After removing the beads, monothiophosphoric acid induced into the substrate was incubated with a 10 mM substrate further labeled with iodoacetyl-biotin (manufactured by Pierce, USA) in a coupling buffer (100 mM Tris-HCl, pH 8.5, 1 mM EDTA) in a dark place at room temperature for 90 minutes, followed by termination of the reaction with β-mercaptoethanol.

The substrate in an amount of 0.4 μg after completing the reaction was added onto a PVDF membrane using a slot blotter, and aspirated. Thus resulting membrane was blocked with 4% bovine serum albumin (BSA) for 30 minutes, and allowed to react with avidin-FITC (manufactured by Vector Laboratories) at 37° C. for 1 hour.

After washing the membrane, images on the membrane were analyzed by a fluorescent image analyzer (manufactured by BioRad). The activity was calculated based on a standard curve corresponding to 0, 12.5, 25, 50, 100 and 150 μg of CDK included in K-562 chronic myeloid leukemia cell strain.

For reference, 1 U means an enzyme activity which is equal to that of K-562 cell with 1 μg of total protein.

3) Measurement of Protein Expression

Surgically collected tissue (2 mm$^3$) was ground with a lysis buffer containing Nonidet P-40 (NP-40), and solubilized by a homogenizer. Insoluble substances were removed with a filter. Then, 2.5 μg of the protein was added to wells (2×2×3 mm, permissible amount: 50 μl) of a slot blotter having a hydrophobic membrane (PVDF, manufactured by Millipore Corporation) set therein. Target substance in the crude sample bound on the membrane was quantitatively detected by the following reaction, i.e., the reaction with an anti-cell cycle related protein antibody, a biotinized secondary antibody and a fluorescent labeled streptavidin.

During each reaction, the wells were automatically washed with TBS (25 mM Tris-HCl, pH 7.4, 150 mM NaCl).

Fluorescent images on the membrane were analyzed by an image analyzer (manufactured by BioRad), and the fluorescent intensity of the dot was measured. Quantitative determination of the cell cycle related protein was carried out with a standard curve obtained using a standard recombinant protein (CDK1; 2.5-25 ng/dot, CDK2; 1.0-10 ng/dot, CDK4; 1.0-10 ng/dot, CDK6; 2.5-25 mg/dot).

EXAMPLE 2

CDK Activity

Each enzyme activity of CDK1, 2, 4 and 6 was measured for gastrointestinal cancer tissues and normal mucosa. Measurement of the activity was conducted with the method described in Example 1, for each of the tissues of (A) large intestine cancer of 22 cases, (B) stomach cancer of 8 cases, and (C) esophagus cancer of 7 cases as well as normal mucosa.

Figure 1:
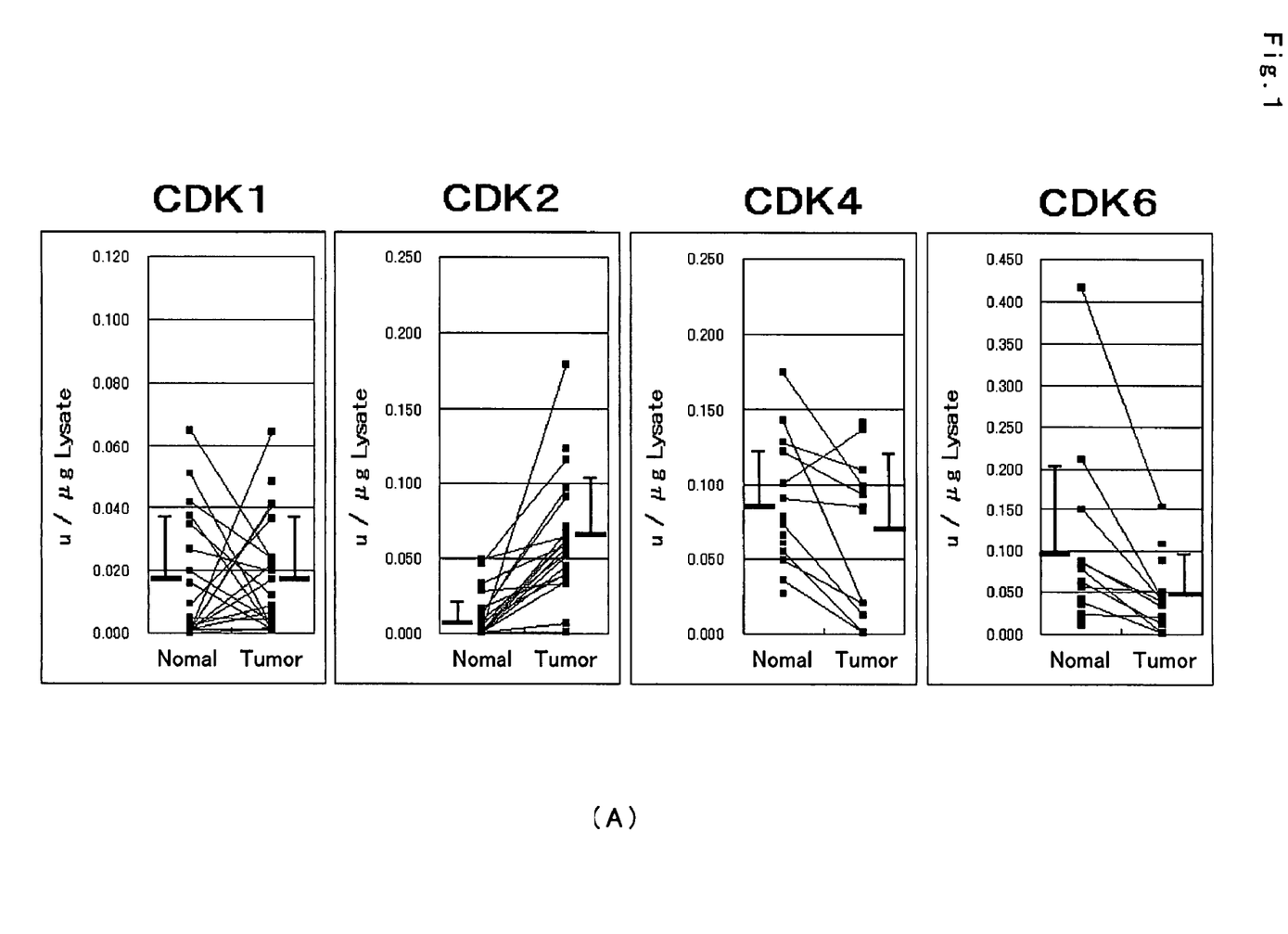
FIG. 1 is a drawing illustrating CDK kinase activities of cancer tissues (A: large intestine cancer, B: stomach cancer, C: esophagus cancer) and normal mucosa. (Example 2)

The results are depicted in FIGS. 1A to C. Consequently, with respect to difference of each enzyme activity between cancer tissues and normal mucosa, statistical significance was found in elevation of the CDK2 activity in the large intestine, stomach and esophagus tissues (P<0.01). On the other hand, CDK4 and CDK6 in the large intestine and stomach cancer tissues exhibited activities that were comparatively lower than those in normal mucosa. Statistical analysis was carried out with a Wilcoxon signed-ranks test. In crease in CDK2 enzyme activity was observed in almost of the large intestine, stomach and esophagus cancer tissues.

EXAMPLE 3

Profile of CDK activity

With respect to CDK (CDK2, 4, 6) in the G1 phase, the activity values of CDK2, 4 and 6 were standardized on the basis of the CDK1 activity value that is G2/M kinase to determine the profile. Consequently, as shown by a solid line in FIG. 2A, in seven among 8 cases of normal large intestine mucosal tissues, CDK profile in the G1 phase positioned in the fold width of 0.024 to 0.43 for CDK2/CDK1, 1.2 to 39 for CDK4/CDK1, and 1.9 to 26 for CDK6/CDK1, exhibiting a common pattern. This suggests that relative values of the CDK activities are similar among the normal large intestine tissues.

Figure 2:
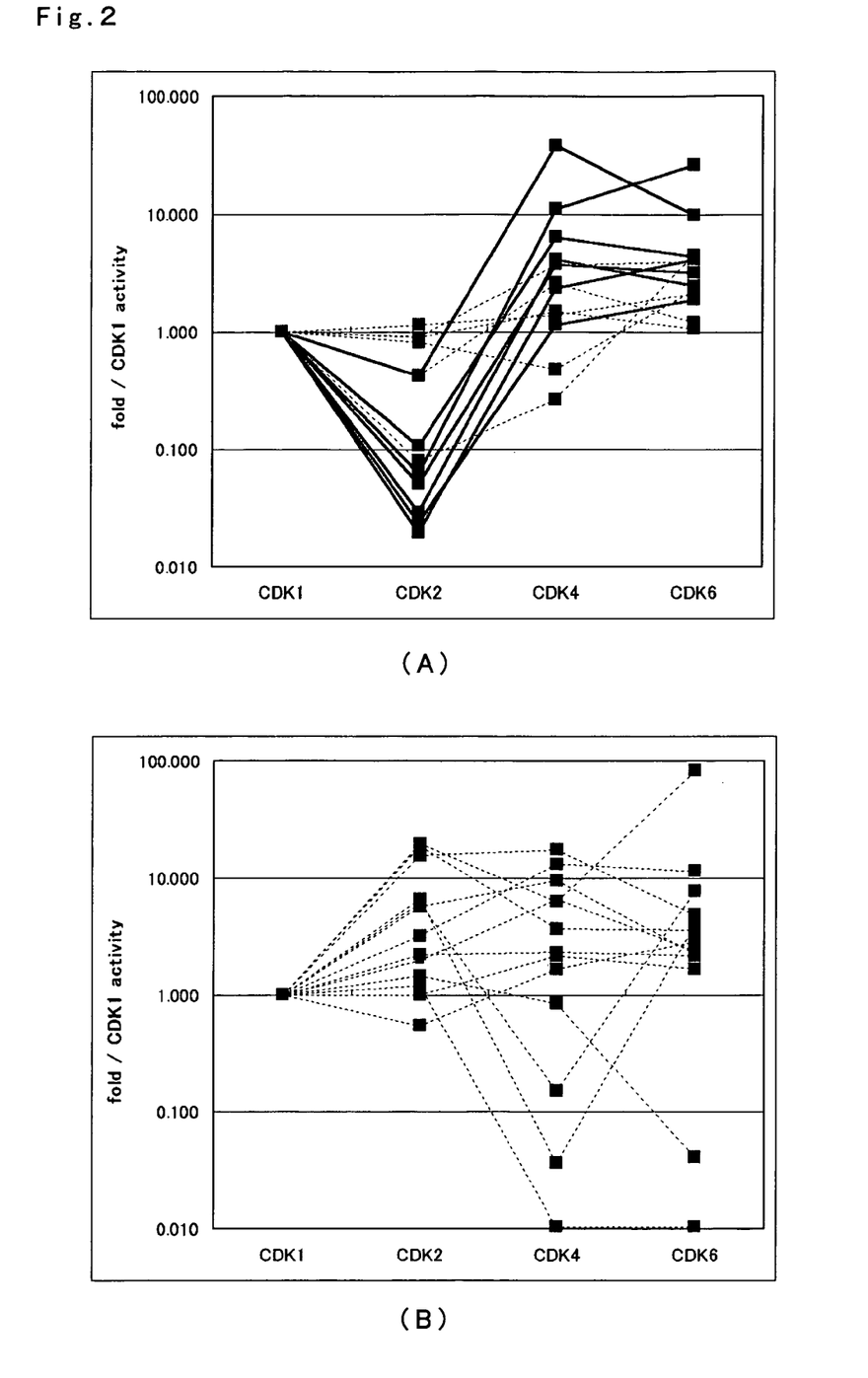
FIGS. 2A and 2B are drawings illustrating profiling of CDK kinase activity. (Example 3)

Next, the profile on the basis of value of CDK1 activity that is G2/M kinase was similarly determined for CDKs (CDK2, 4, 6) in the G1 phase on randomly selected nine cases of large intestine cancer tissue. Consequently, as shown in FIG. 2B, no profile was observed which was identical to the common profile found in the normal mucosal tissues According to the present invention, it was found that more accurate examination of cancer tissues and cancer cells is possible when cell cycle profiling that involves measurement of the activity is carried out. It is expected that high probability to result in a prognostic factor would be found on analyses of expression, activity, and profiling and the like of each cell cycle regulation factor in retrospective or prospective tests.

In addition, the method of the present invention in which cell cycle profiling that involves measurement of the activity is carried out will be extremely valuable one which can be adapted to tailor made medical treatments, because it was reported in connection with breast cancer that expression of an isomer of cyclin E that imparts excessive activity to CDK2 strongly correlates to survival rate of patients.

INDUSTRIAL APPLICABILITY

When the cell cycle profiling that involves measurement of the activity is carried out according to the method of the present invention, more accurate examination of cancer tissues and cancer cells can be executed, and definite diagnosis of cancer, drug resistance test and prognosis are enabled.

TABLE 1

Clinicopathological features of patients

| Patieut | Sex | Age | Stage | Tissue-type | Site | Metastasis Lymph-node | Peritoneum | Liver | Distant | Invasion |
|---|---|---|---|---|---|---|---|---|---|---|
| | | | | Colon cancer | | | | | | |
| C001 | F | 53 | IIIb | well/mod | As | N2 | P0 | H0 | M0 | V1 Ly1 |
| C002 | M | 66 | I | well/mod | Rs | N0 | P0 | H0 | M0 | V3 Ly1 |
| C003 | M | 67 | IIIa | well/mod | Rs-S | N1 | P0 | H0 | M0 | V1 Ly1 |
| C005 | M | 56 | IIIb | mod-por | Ac | N2 | P0 | H0 | M0 | V1 Ly1 |
| C006 | M | 48 | IIIa | well-mod | Rb | N0 | P0 | H0 | M0 | V1 Ly1 |
| C007 | F | 80 | IIIa | ne | Rb | N1 | P0 | H0 | M0 | V1 Ly2 |
| C008 | M | 73 | II | muc | A | N0 | P0 | H0 | M0 | V0 Ly1 |
| C009 | M | 60 | I | well/mod | Rs | N0 | P0 | H0 | M0 | V1 Ly0 |
| C010 | M | 83 | IIIb | well/mod | T | N2 | P0 | H0 | M0 | V2 Ly1 |
| C011 | M | 77 | IIIa | well/mod | Rs | N1 | P0 | H0 | M0 | V2 Ly1 |
| C012 | M | 86 | IIIa | well/mod | Rb | N1 | P0 | H0 | M0 | V2 Ly1 |
| C013 | F | 71 | I | por > mod | A | N0 | P0 | H0 | M0 | V0 Ly1 |
| C014 | F | 81 | II | well/mod | Rs | N0 | P0 | H0 | M0 | V0 Ly1 |
| C015 | F | 70 | III | well/mod | Rab | N1 | P0 | H0 | M0 | V1 Ly2 |
| C016 | F | 43 | IV | well | S | N1 | P0 | H0 | M1 | V1 Ly1 |
| C017 | M | 47 | II | well/mod | RaRs | N0 | P0 | H0 | M0 | V2 Ly1 |
| C018 | M | 59 | II | well/mod | Rs | N0 | P0 | H0 | M0 | V1 Ly1 |
| C019 | F | 34 | IIIa | well/mod | Re | N1 | P0 | H0 | M0 | V1 Ly1 |
| C020 | M | 73 | II | well/mod | A | N0 | P0 | H0 | M0 | V1 Ly1 |
| C021 | M | 48 | IIIb | mod-por | Ds | N2 | P0 | H0 | M0 | V3 Ly3 |
| C022 | M | 23 | IIIb | por | Ce | N3 | P0 | H0 | M0 | V1 Ly1 |
| C023 | F | 79 | II | well/mod | Rs | N0 | P0 | H0 | M0 | V1 Ly1 |

TABLE 1-continued

Clinicopathological features of patients

| Patient | Sex | Age | Stage | Tissue-type | Site | Metastasis Lymph-node | Peritoneum | Liver | Distant | Invasion |
|---|---|---|---|---|---|---|---|---|---|---|
| *Gastric cancer* | | | | | | | | | | |
| S001 | M | 70 | IV | tub2 | Ue | N2 | P0 | H1 | M0 | V1 Ly1 |
| S002 | M | 66 | IIIb | por > tub2 | Ue | N2 | P0 | H0 | M0 | V1 Ly1 |
| S005 | M | 59 | Ib | tub1–2 | U | N0 | P0 | H0 | M0 | V2 Ly2 |
| S006 | F | 67 | IV | por2 | Lm | N2 | P1 | H0 | M0 | V3 Ly3 |
| S008 | M | 75 | IV | tub2 > por1 | L | N2 | P0 | H1 | M0 | V3 Ly3 |
| S009 | M | 67 | IV | tub2 | M | N3 | P0 | H1 | M0 | V2 Ly2 |
| S010 | M | 72 | IV | tub2 > por | Ml | N2 | P0 | H1 | M1 | V2 Ly3 |
| S011 | F | 40 | II | muc | M | N1 | P0 | H0 | M0 | V0 Ly2 |
| *Esophageal carcinoma* | | | | | | | | | | |
| E002 | M | 46 | IVa | por >> mod | Lt-Ae | N2 | | | M0 | V1 Ly1 |
| E003 | M | 77 | IVb | mod | Lt | N3 | | | M1 | V2 Ly2 |
| E005 | M | 44 | III | mod > well | MtLt | N3 | | | M0 | V1 Ly2 |
| E006 | M | 60 | III | mod > por | UtLt | N1 | | | M0 | V0 Ly2 |
| E008 | M | 61 | IVa | mod | Mt | N2 | | | M0 | V2 Ly2 |
| E009 | M | 65 | II | well | Mt | N1 | | | M0 | V1 Ly1 |
| E010 | M | 59 | III | mod > por | Ae | N3 | | | M0 | V1 Ly1 |

TABLE 2

Each CDK activity in colon cancer patients

| Sample name | cdk1 kinase (U/ug lysate) | cdk2 kinase (U/ug lysate) | cdk4 kinase (U/ug lysate) | cdk6 kinase (U/ug lysate) |
|---|---|---|---|---|
| C001 | 0.000 | 0.056 (+) | 0.082 | 0.041 |
| C002 | 0.049 | 0.072 (+) | | |
| C003 | 0.065 (+) | 0.065 (+) | 0.141 | 0.109 |
| C005 | 0.024 | 0.097 (+) | | |
| C006 | 0.042 | 0.117 (+) | | |
| C007 | 0.020 | 0.057 (+) | | |
| C008 | 0.008 | 0.124 (+) | 0.138 | 0.039 |
| C009 | 0.001 | 0.038 | | |
| C010 | 0.000 | 0.179 (+) | | |
| C011 | 0.004 | 0.062 (+) | | |
| C012 | 0.024 | 0.034 | 0.020 (−) | (0.032) (−) |
| C013 | 0.000 | 0.059 (+) | (0.094) (−) | (0.035) (−) |
| C014 | 0.037 | 0.068 (+) | | |
| C015 | 0.022 | 0.053 (+) | | |
| C016 | 0.009 | 0.051 (+) | 0.085 | 0.021 |
| C017 | 0.041 | 0.091 (+) | 0.095 | 0.089 |
| C018 | 0.017 | 0.033 | 0.110 | 0.040 |
| C019 | 0.000 | 0.045 (+) | 0.099 | 0.154 |
| C020 | 0.007 | 0.040 | (0.003) (−) | 0.050 |
| C021 | 0.012 | 0.007 | 0.020 (−) | 0.034 |
| C022 | 0.003 | 0.063 (+) | 0.012 (−) | 0.012 |
| C023 | 0.001 | 0.000 | 0.093 | 0.042 |

TABLE 3

Amount of each protein expression in colon cancer patient

| Sample name | cdk1 (ng/ug lysate) | cdk2 (ng/ug lysate) | cdk4 (ng/ug lysate) | cdk6 (ng/ug lysate) | cyclinD1 (ng/ug lysate) |
|---|---|---|---|---|---|
| C001 | 1.285 | 0.263 | 0.620 | 0.278 | 0.052 |
| C002 | 2.822 (+) | 0.519 | 0.989 (+) | 0.579 | 0.123 |
| C003 | 1.392 | 0.367 | 0.777 | 0.307 | 0.051 |
| C005 | 2.606 (+) | 0.492 | 0.970 (+) | 0.405 | 0.089 |
| C006 | 1.618 | 0.000 | 0.343 | 0.000 | 0.077 |
| C007 | 2.363 (+) | 0.349 | 0.640 | 0.309 | 0.053 |
| C008 | 3.022 (+) | 0.359 | 0.567 | 0.538 | 0.093 |
| C009 | 0.000 (−) | 0.000 | 0.000 (−) | 0.000 | 0.000 (−) |
| C010 | 2.058 (+) | 0.000 | 0.379 | 0.373 | 0.076 |
| C011 | 1.093 | 0.227 | 0.492 | 0.000 | 0.095 |
| C012 | 0.673 | 0.164 | 0.348 | 0.000 | 0.046 |
| C013 | 1.567 | 0.225 | 0.437 | 0.334 | 0.077 |
| C014 | 1.444 | 0.209 | 0.766 | 0.385 | 0.143 |
| C015 | 0.869 | 0.000 | 0.192 | 0.000 | 0.074 |
| C016 | 1.417 | 0.200 | 0.866 (+) | 0.806 (+) | 0.115 |
| C017 | 0.824 | 0.000 | 0.486 | 0.000 | 0.058 |
| C018 | 0.917 | 0.000 | 0.299 | 0.000 | 0.075 |
| C019 | 0.981 | 0.000 | 0.570 | 0.000 | 0.073 |

TABLE 3-continued

Amount of each protein expression in colon cancer patient

| | | | | | |
|---|---|---|---|---|---|
| C020 | 0.800 | 0.194 | 0.149 | 0.000 | 0.041 |
| C021 | 0.910 | | 0.551 | | 0.064 |
| C022 | 1.991 (+) | 0.343 | 0.531 | 0.422 | 0.075 |
| C023 | 0.800 | 0.202 | 0.517 | 0.000 | 0.069 |

| Sample name | cyclinE (ng/ug lysate) | p53 ELISA (pg/ug lysate) | p21 ELISA (mU/ug lysate) | p16 WB (CNT × mm) | p27 (ng/ug lysate) |
|---|---|---|---|---|---|
| C001 | 0.501 | | | | 0.134 |
| C002 | 0.561 | 0.162 | | | 0.133 |
| C003 | 0.433 | 1.355 (+) | 2.600 (−) | | 0.123 |
| C005 | 0.762 | 0.162 | 7.070 | | 0.152 |
| C006 | 0.427 | 1.768 (+) | 5.696 | | 0.089 |
| C007 | 0.319 | 1.010 (+) | 3.890 | 61.2 (+) | 0.128 |
| C008 | 0.691 | 0.513 (+) | 12.690 | 107.5 (+) | 0.114 |
| C009 | 0.000 (−) | 0.077 (−) | 4.804 | | 0.000 (−) |
| C010 | 0.303 | 0.054 (−) | 5.607 | | 0.117 |
| C011 | 0.000 (−) | 0.365 (+) | 1.554 (−) | | 0.158 |
| C012 | 0.000 (−) | 0.339 (+) | 3.290 | 37.5 | 0.000 (−) |
| C013 | 0.429 | 0.178 | 8.160 | 21.6 | 0.166 |
| C014 | 0.371 | 0.067 (−) | 8.034 | | 0.091 |
| C015 | 0.501 | 0.057 (−) | 1.178 (−) | | 0.066 |
| C016 | 0.482 | 0.171 | 3.470 | 130.2 (+) | 0.107 |
| C017 | 0.425 | 0.226 | | | 0.084 |
| C018 | 1.480 | 0.193 | 4.250 | 35.2 | 0.160 |
| C019 | 0.618 | 2.963 (+) | 6.970 | 18.2 | 0.089 |
| C020 | 1.054 | 0.247 (+) | 5.030 | 29.7 | 0.220 |
| C021 | 1.411 | 0.180 | 5.010 | 31.7 | 0.397 |
| C022 | 0.468 | 0.224 | 7.890 | 25.4 | 0.128 |
| C023 | 0.494 | 0.223 | 12.720 | 19.7 | 0.198 |

TABLE 4

Each CDK activity in gastric cancer patient

| Sample name | cdk1 kinase (U/ug lysate) | cdk2 kinase (U/ug lysate) | cdk4 kinase (U/ug lysate) | cdk6 kinase (U/ug lysate) |
|---|---|---|---|---|
| S001 | 0.096 | 0.116 (+) | (0.014) | (0.038) (−) |
| S002 | 0.011 | 0.014 | | |
| S005 | 0.074 | 0.129 (+) | | |
| S006 | 0.000 | 0.182 (+) | 0.015 | 0.038 (−) |
| S008 | 0.027 | 0.181 (+) | (0.012) | 0.108 |
| S009 | 0.000 | 0.555 (+) | 0.067 | 0.024 (−) |
| S010 | 0.000 | 0.226 (+) | 0.037 | 0.101 |
| S011 | 0.000 | 0.030 | 0.040 | 0.041 (−) |

TABLE 5

Amount of each protein expression in gastric cancer patient

| Sample name | cdk1 (ng/ug lysate) | cdk2 (ng/ug lysate) | cdk4 (ng/ug lysate) | cdk6 (ng/ugl lysate) | cyclinD1 (ng/ug lysate) |
|---|---|---|---|---|---|
| S001 | 1.727 | 0.504 | 0.813 | 0.584 | 0.105 |
| S002 | 6.960 (+) | 2.232 (+) | 2.255 (+) | 3.627 (+) | 0.256 (+) |
| S005 | 1.035 | 0.000 (−) | 0.282 | 0.000 (−) | 0.051 |
| S006 | 2.524 (+) | 0.377 | 0.645 | 0.514 | 0.083 |
| S008 | 3.023 (+) | 0.404 | 1.536 (+) | 0.376 | 0.195 (+) |
| S009 | 2.155 (+) | 0.330 | 0.405 | 0.451 | 0.044 |
| S010 | 4.278 (+) | 0.343 | 0.690 | 0.518 | 0.103 |
| S011 | 0.713 | 0.000 (−) | 0.208 | 0.000 (−) | 0.057 |

| Sample name | cyclinE (ng/ug lysate) | p53 ELISA (pg/ug lysate) | p21 ELISA (mU/ug lysate) | p16 WB (CNT × mm) | p27 (ng/ug lysate) |
|---|---|---|---|---|---|
| S001 | 0.518 | 0.158 | 4.050 | 58.0 (+) | 0.141 |
| S002 | 3.692 (+) | 0.182 | 8.550 | | 0.566 (+) |
| S005 | 0.300 | 1.279 | 3.824 | | 0.109 |
| S006 | 0.840 | 3.431 (+) | 8.270 | 78.4 (+) | 0.138 |
| S008 | 0.298 | 2.236 (+) | 7.065 | 92.3 (+) | 0.077 |
| S009 | 0.600 | 0.980 | 3.050 | 72.7 (+) | 0.107 |

TABLE 5-continued

Amount of each protein expression in gastric cancer patient

| S010 | 0.420 | 0.104 | 16.560 (+) | 68.4 (+) | 0.096 |
| S011 | 0.312 | 0.000 | 1.150 | 16.7 | 0.086 |

TABLE 6

Each CDK activity in esophageal cancer patient

| Sample name | cdk1 kinase (U/ug lysate) | cdk2 kinase (U/ug lysate) | cdk4 kinase (U/ug lysate) | cdk6 kinase (U/ug lysate) |
| --- | --- | --- | --- | --- |
| E002 | 0.000 | 0.073 (+) | 0.125 | 0.149 |
| E003 | 0.000 | 0.034 | | |
| E005 | 0.000 | 0.089 (+) | | |
| E006 | 0.000 | 0.047 (+) | | |

TABLE 6-continued

Each CDK activity in esophageal cancer patient

| Sample name | cdk1 kinase (U/ug lysate) | cdk2 kinase (U/ug lysate) | cdk4 kinase (U/ug lysate) | cdk6 kinase (U/ug lysate) |
| --- | --- | --- | --- | --- |
| E008 | 0.000 | 0.033 | | |
| E009 | 0.012 (+) | 0.037 (+) | 0.154 | 0.133 |
| E010 | 0.002 | 0.048 (+) | 0.015 | 0.201 |

TABLE 7

Amount of each protein expression in esophageal carcinoma patient

| Sample name | cdk1 (ng/ug lysate) | cdk2 (ng/ug lysate) | cdk4 (ng/ug lysate) | cdk6 (ng/ug lysate) | cyclinD1 (ng/ug lysate) |
| --- | --- | --- | --- | --- | --- |
| E002 | 2.524 (+) | 0.377 (+) | 0.645 | 0.514 (+) | 0.083 |
| E003 | 1.742 (+) | 0.255 | 0.392 | 0.000 | 0.093 |
| E005 | 3.240 (+) | 0.324 (+) | 1.095 | 0.567 (+) | 0.168 |
| E006 | 0.841 | 0.000 | 0.674 | 0.345 (+) | 0.055 |
| E008 | 0.484 | 0.000 | 0.000 (−) | 0.000 | 0.000 (−) |
| E009 | 0.875 | 0.000 | 0.169 | 0.000 | 0.033 (−) |
| E010 | 1.092 (+) | 0.277 | 0.306 | 0.344 (+) | 0.060 |

| Sample name | cyclinE (ng/ug lysate) | p53 ELISA (pg/ug lysate) | p21 ELISA (mU/ug lysate) | p16 WB (CNT × mm) | p27 (ng/ug lysate) |
| --- | --- | --- | --- | --- | --- |
| E002 | 0.840 (+) | | | 3.9 | 0.138 |
| E003 | 0.391 (+) | 0.099 | 10.749 (+) | | 0.081 |
| E005 | 0.310 (+) | 0.141 | 8.032 (+) | | 0.073 |
| E006 | 0.313 (+) | 0.240 | 11.526 (+) | | 0.088 |
| E008 | 0.000 (−) | 0.104 | 4.842 | | 0.000 (−) |
| E009 | 0.000 (−) | 0.247 | 5.750 | | 0.066 |
| E010 | 0.000 (−) | 0.126 | 8.560 (+) | | 0.083 |

TABLE 8

| | CDK1 | | CDK2 | | CDK4 | | CDK6 | |
| --- | --- | --- | --- | --- | --- | --- | --- | --- |
| | Nomal | Tumor | Nomal | Tumor | Nomal | Tumor | Nomal | Tumor |
| Activity (U/μg total protein ± s.d.) | | | | | | | | |
| Colon | 0.017 ± 0.020 | 0.017 ± 0.019 | 0.012 ± 0.016 | 0.065 ± 0.040 | 0.086 ± 0.043 | 0.069 ± 0.051 | 0.094 ± 0.11 | 0.049 ± 0.044 |
| Stomac | 0.034 ± 0.036 | 0.027 ± 0.038 | 0.040 ± 0.031 | 0.18 ± 0.17 | 0.10 ± 0.086 | 0.027 ± 0.026 | 0.10 ± 0.050 | 0.052 ± 0.043 |
| Esophagus | 0.004 ± 0.003 | 0.003 ± 0.004 | 0.011 ± 0.011 | 0.055 ± 0.022 | 0.098 | 0.098 ± 0.073 | 0.16 | 0.16 ± 0.036 |
| Expession (ng/μg total protein ± s.d.) | | | | | | | | |
| Colon | 0.79 ± 0.60 | 1.5 ± 0.78 | 0.23 ± 0.24 | 0.21 ± 0.17 | 0.35 ± 0.23 | 0.54 ± 0.25 | 0.19 ± 0.23 | 0.24 ± 0.25 |
| Stomac | 0.84 ± 0.38 | 2.8 ± 2.0 | 0.39 ± 0.29 | 0.52 ± 0.71 | 0.38 ± 0.17 | 0.85 ± 0.70 | 0.28 ± 0.26 | 0.76 ± 1.2 |
| Esophagus | 0.63 ± 0.14 | 1.7 ± 1.0 | 0.084 ± 0.11 | 0.21 ± 0.16 | 0.59 ± 0.39 | 0.55 ± 0.33 | 0.001 | 0.30 ± 0.25 |

The invention claimed is:

1. A method of diagnosing a cell for cancer comprising:
   measuring a first activity value of CDK1 and a second activity value of CDK2 in a cell collected from a patient;
   obtaining a first relative activity value represented by a ratio of the second activity value to the first activity value;
   producing a cell cycle profile on the basis of the obtained first relative activity value;
   comparing the produced cell cycle profile with a cell cycle profile of a normal cell; and
   determining that the cell collected from the patient is a cancer cell, when a statistically significant difference between the produced cell cycle profile and the cell cycle profile of a normal cell exists.

2. The method according to claim 1, wherein the measuring step is performed by further measuring a third activity value of CDK4, the obtaining step is performed by further obtaining a second relative activity value represented by a ratio of the third activity value to the first activity value, and the producing step is performed by producing the cell cycle profile on the basis of the first and second relative activity values.

3. The method according to claim 1, wherein the measuring step is performed by further measuring a fourth activity value of CDK6, the obtaining step is performed by further obtaining a third relative activity value represented by a ratio of the fourth activity value to the first activity value, and the producing step is performed by producing the cell cycle profile on the basis of the first and third relative activity values.

4. The method according to claim 1, wherein the measuring step is performed by further measuring a third activity value of CDK4 and a fourth activity value of CDK6, the obtaining step is performed by further obtaining a second relative activity value represented by a ratio of the third activity value to the first activity value and a third relative activity value represented by a ratio of the fourth activity value to the first activity value, and the producing step is performed by producing the cell cycle profile on the basis of the first, second and third relative activity values.

5. The method according to claim 1, wherein the measuring step is performed by further measuring an expression amount of a cyclin.

6. The method according to claim 1, wherein the measuring step is performed by further measuring an expression amount of a cyclin dependent kinase inhibitor.

7. The method according to claim 1, wherein the statistically significant difference is based on a Wilcoxon signed-ranks test.

8. A method of diagnosing a cell for cancer comprising:
   measuring a first activity value of CDK1 and a second activity value of CDK2 in a cell collected from a patient;
   obtaining a first relative activity value represented by a ratio of the second activity value to the first activity value;
   comparing the first relative activity value with that of a normal cell; and
   determining that the cell collected from the patient is a cancer cell, when a statistically significant difference between the obtained first relative activity value and that of a normal cell exists.

9. The method according to claim 8, wherein the measuring step is performed by further measuring a third activity value of CDK4, the obtaining step is performed by further obtaining a second relative activity value represented by a ratio of the third activity value to the first activity value, and the comparing step is performed by comparing the first and second relative activity values with that of the normal cell.

10. The method according to claim 8, wherein the measuring step is performed by further measuring a fourth activity value of CDK6, the obtaining step is performed by further obtaining a third relative activity value represented by a ratio of the fourth activity value to the first activity value, and the comparing step is performed by comparing the first and third relative activity values with that of the normal cell.

11. The method according to claim 8, wherein the measuring step is performed by further measuring a third activity value of CDK4 and a fourth activity value of CDK6, the obtaining step is performed by further obtaining a second relative activity value represented by a ratio of the third activity value to the first activity value and a third relative activity value represented by a ratio of the fourth activity value to the first activity value, and the comparing step is performed by comparing the first, second and third relative activity values with that of the normal cell.

12. The method according to claim 8, wherein the measuring step is performed by further measuring an expression amount of a cyclin.

13. The method according to claim 8, wherein the measuring step is performed by further measuring an expression amount of a cyclin dependent kinase inhibitor.

14. The method according to claim 8, wherein the statistically significant difference is based on a Wilcoxon signed-ranks test.

* * * * *